United States Patent [19]

Higuchi et al.

[11] Patent Number: 5,589,390

[45] Date of Patent: Dec. 31, 1996

[54] VERMIN EXTERMINATING ELEMENT AND VERMIN EXTERMINATING METHOD

[75] Inventors: Toshio Higuchi; Yasuhiro Fukushima; Kenji Furumori; Kazuhiro Yamamoto; Minoru Ouchi, all of Osaka, Japan

[73] Assignee: Nitto Denko Corporation, Osaka, Japan

[21] Appl. No.: 479,840

[22] Filed: Jun. 7, 1995

Related U.S. Application Data

[63] Continuation of Ser. No. 124,435, Sep. 22, 1993, abandoned, which is a continuation of Ser. No. 7,015, Jan. 21, 1993, abandoned, which is a continuation of Ser. No. 700,151, filed as PCT/JP90/01140, Sep. 5, 1991, published as WO91/03545, Mar. 21, 1991, abandoned.

[30] Foreign Application Priority Data

Sep. 11, 1989 [JP] Japan ..................... 1-234969
Mar. 23, 1990 [JP] Japan ..................... 2-74598

[51] Int. Cl.⁶ ................. C12N 1/00; C12M 1/00
[52] U.S. Cl. .............. 435/307.1; 435/174; 435/180; 424/403; 424/411; 424/413; 424/419; 43/124; 43/132.1
[58] Field of Search ................. 435/284, 285, 435/287, 292, 293, 299, 283.1, 309.1, 307.1, 174, 180; 422/56, 57, 60; 424/403, 411, 413, 419; 43/124, 131, 132.1, 136

[56] References Cited

U.S. PATENT DOCUMENTS

| | | | |
|---|---|---|---|
| 2,017,159 | 10/1935 | Mucha | 43/124 |
| 3,295,246 | 1/1967 | Landsman et al. | 43/131 |
| 3,864,468 | 2/1975 | Hyman et al. | 424/16 |
| 3,881,993 | 5/1975 | Freake et al. | 435/292 |
| 4,565,783 | 1/1986 | Hansen et al. | 435/299 |
| 4,796,381 | 1/1989 | Kauth et al. | 43/124 |
| 4,921,703 | 5/1990 | Higuchi et al. | 424/419 |
| 5,264,129 | 11/1993 | Simpson et al. | 435/310 |

FOREIGN PATENT DOCUMENTS

| | | | |
|---|---|---|---|
| 15-004038 | 3/1940 | Japan . | |
| 60-214878 | 10/1985 | Japan . | |
| 61-033554 | 8/1986 | Japan . | |
| 232377 | 10/1987 | Japan . | |
| 62-232377 | 10/1987 | Japan . | |
| 63-000403 | 1/1988 | Japan . | |
| 63-074479 | 4/1988 | Japan . | |
| 190807 | 8/1988 | Japan . | |
| 63-010807 | 8/1988 | Japan . | |
| 3196277 | 8/1988 | Japan | 435/284 |
| WO87006955 | 11/1987 | WIPO . | |

Primary Examiner—Robert J. Warden
Assistant Examiner—Theresa T. Snider
Attorney, Agent, or Firm—Sughrue, Mion, Zinn, Macpeak & Seas

[57] ABSTRACT

A vermin exterminating element contains a culture carrier which includes nonwoven cloth or woven cloth coated or impregnated with medium components for cultivating a microorganism and with a culture solution of a vermin infectious microorganism, wherein the vermin exterminating element is dried after cultivating the vermin infectious microorganism, and the nonwoven cloth or woven cloth has a thickness of 1.8 mm or more and has a base weight of at least 100 g/m².

19 Claims, 1 Drawing Sheet

VERMIN EXTERMINATING ELEMENT AND VERMIN EXTERMINATING METHOD

This is a Continuation of application No. 08/124,435, filed Sep. 22, 1993, which is a Continuation of application No. 08/007,015, filed Jan. 21, 1993, which is a Continuation of application No. 07/700,151, filed as PCT/JP90/01140, Sep. 5, 1991, published as WO91/03545, Mar. 21, 1991, all abandoned.

FIELD OF THE INVENTION

The present invention relates to a culture carrier for cultivating microorganisms and a vermin exterminating element using the same as well as a method for exterminating vermin.

BACKGROUND

For cultivation of a microorganism, there are heretofore known liquid culture and solid culture using rice bran, etc. These techniques are used alone or in combination, depending upon, e.g., kind of cells, metabolites, etc.

In a liquid culture, however, proliferation of pellets occurs during cultivation so that the cultivation efficiency of the microorganism decreases. Further, in a solid culture, it is difficult to isolate the product produced depending on microorganism used. Both culture techniques are disadvantageous in these regards.

In order to eliminate such drawbacks, there is proposed a method for cultivation by carrying medium components on a foam. For example, in Japanese Published Examined Patent Application No. 55-36313, a technique is shown which comprises impregnating a foam such as sponge, etc. with medium components and then performing a stationary culture. According to this technique, however, there is a limit in the amounts of the medium components to be impregnated. An impregnation rate is approximately 30 to 50 wt % with, e.g., commercially available polyurethane foam and about 90 wt %, even with a foam having a good impregnation property. Accordingly, a medium satisfactory for cultivation of a microorganism is not formed and effective cultivation is made only with difficulty. In addition, such a foam is extremely readily dried so that the foam is not always a good material to use for cultivation of a microorganism.

On the other hand, various techniques are proposed for liquid culture; for example, a method which comprises incorporating a large number of foam pieces (Japanese Published Unexamined Patent Application No. 60-214878), a method which comprises using a hydrophilic foam having formed a peptide matrix in the molecule thereof (Japanese Published Examined Patent Application No. 53-11316), a method which comprises using a foam for cultivating a microorganism, in a matrix of which foam medium components are contained (Japanese Published Unexamined Patent Application No. 63-74479), etc.

In these foams, however, the microorganism is cultured only on the surface of each foam so that the ratio of surface area to apparent volume is small, showing the tendency of a decrease in cultivation efficiency. Furthermore, since it is difficult to incorporate medium components only into the surface of foam, amounts of medium components more than required are necessary and such is disadvantageous from an economical viewpoint. Moreover, it is necessary to perform a sterilization treatment thereby to prevent contamination of the aforesaid foam with other bacteria until the foam is provided for use; however, at heat sterilization above 100° C., the foam itself is denatured so that costly steam sterilization or gas sterilization is required.

On the other hand, molds such as *Beauveria tenella*, etc. are present as a natural enemy of longicorn beetles, gold beetles, whiteflies, rice insects, leafhoppers, etc. which damage various agricultural crops or trees. Using these natural enemy molds, various methods for terminating vermin have been proposed.

For example, Japanese Published Examined Patent Application No. 63-403 discloses a method which comprises directly sprinkling bacteria cultured in bran medium over trees together with medium. According to this method, however, the bacteria cannot utilize medium components sufficiently, but the bacteria are in a state such that they are close to dormant cells. Accordingly, an expected insecticidal effect is not exhibited sometimes. In addition, the method for extermination relies on sprinkling so that the bacteria adhere to trees only with difficulty, resulting in a poor insecticidal efficiency.

In order to solve these defects, Japanese Published Unexamined Patent Application No. 63-19080 proposes an elastic carrier such as a foam having cultured therein bacteria for infection. While the above defects are solved, however, the bacteria are not sufficiently closely adhered to the amorphous surface of trees, etc., even though they are disposed onto the surface thereof. Thus, the problem still remains unsolved. Where cardboard or the like is used as a carrier, it is preferred in view of natural degradation but has a poor mechanical strength so that a problem of breakage during use is involved.

The present invention has been made to solve the problems of the prior art described above and an object is to provide a culture carrier for cultivating microorganisms which can effectively incubate the microorganism.

Another object of the present invention is to provide a vermin exterminating element using the carrier described above.

A further object of the present invention is to provide a method for terminating vermin using the vermin exterminating element described above.

DISCLOSURE OF THE INVENTION

As a result of investigations to achieve the objects described above, the present inventors have found that by using nonwoven cloth or woven cloth having a large apparent surface area as a base material for cultivation of microorganism, medium components can be incorporated effectively and a cultivation efficiency also becomes high, and have come to accomplish the present invention.

That is, the present invention relates to a culture carrier for cultivating microorganisms comprising nonwoven cloth or woven cloth having incorporated therein medium components for cultivating the microorganism, and a vermin exterminating element comprising the culture carrier for cultivating microorganisms having cultivated therein bacteria for infecting vermin. Particularly by incorporating a hydrophilic polymer into the nonwoven cloth described above, the water retaining ability is improved and a cultivation efficiency is further enhanced. From the viewpoint of storage, the vermin exterminating element is preferably dried. The present invention also provides a method for extermination of vermin which comprises applying the vermin exterminating element described above to the stem or branch of trees from which vermin are to be exterminated.

Materials of the nonwoven cloth or woven cloth which are used as the carrier in the present invention are not particularly limited but any commercially available materials may be used. In view of impregnation property of medium components, the thickness of the nonwoven cloth or woven cloth is preferably as thin as possible, generally about 0.3 mm or thicker, preferably about 0.5 to about 2 mm. The base weight of the nonwoven cloth or woven cloth is generally at least 20 g/m², preferably in a range of 40 to 500 g/m², more preferably in a range of 100 to 200 g/m².

Of these carriers, those composed of materials such as pulp, rayon, polyester, etc. are particularly preferred from the standpoint of impregnation ability of medium components, adherence to microorganism, utilizability as carbon sources and natural degradation property. These materials are also hydrophilic and have a good water retaining property. It is particularly preferable to use pulp materials.

The medium components which are incorporated into the nonwoven cloth or woven cloth are assimilable carbon sources and inorganic salts or natural organics as nitrogen sources. Examples of the carbon sources include glucose, saccharose, lactose, maltose, glycerine, starch, cellulose, molasses, etc. Examples of the inorganic salts which are used as nitrogen sources include ammonium sulfate, ammonium chloride, ammonium nitrate, etc. Examples of the natural organics include extracts or ground products of animal tissue such as meat extract, fish meat extract, chrysalis powders, etc.; bacterial cells or extracts thereof such as dry yeast, yeast extract, polypeptone, etc. In addition to inorganic salts other than the nitrogen sources, for example, potassium dihydrogenphosphate, magnesium sulfate, calcium sulfate, potassium sulfate, etc. may also be incorporated.

The culture carrier for cultivating microorganisms in accordance with the present invention is obtained by coating the medium components for cultivation of microorganism directly to the nonwoven cloth or woven cloth described above or impregnating the nonwoven cloth or woven cloth with the medium components. The nonwoven cloth or woven cloth used may not be always single but a plurality of the nonwoven cloth or woven cloth may also be laminated on each other. Where the nonwoven cloth or woven cloth is laminated to make the culture carrier of the present invention for cultivation of microorganism, the medium components described above are coated onto the surface of each carrier layer, whereby the medium components function as adhesive components between the layers. Most of the medium components are relatively viscous so that they sufficiently function as adhesive agents.

In the case that the medium components are so utilized as adhesives for lamination of the nonwoven cloth or woven cloth, the viscosity of the medium components is adjusted to at least 10 centipoise, preferably in a range of $10^2$ to $10^4$ centipoise. The content of the medium components is at least 10 g, preferably 20 to 70 g, per m² of the carrier. Where the content is less than 10 g, a microorganism cultured grows insufficiently; when the content exceeds 70 g, an amount of growth reaches its saturation and uneconomical. The amount of growth is about $10^8$ cells per cm² of the carrier. The count of conidia is constant.

In order to improve the hydrophilic property of the culture carrier for cultivating microorganisms and enhance the water retention property in the present invention, it is preferred to incorporate approximately 1 to 10 wt % of the hydrophilic polymer into the carrier. By incorporating the hydrophilic polymer, the content of the medium components increases by about twice. Further, where the medium components are used as adhesive components and utilized for lamination of the nonwoven cloth or woven cloth, incorporation of the hydrophilic polymer into the medium components results an increase in the viscosity of medium components. Thus, an adhesive effect is improved.

Examples of such hydrophilic polymer include agar, polyvinyl alcohol, polyacrylamide, starch, konjak mannan, carboxymethyl cellulose, polyacrylic acid (including salts thereof), polyacrylonitrile, alginic acid (including salts thereof), etc. In order to enhance the water retention property and increase the content of medium components, a hydrophilic polymer which is a highly water absorbing polymer and which swells but does not dissolve in water may also be incorporated. Examples of the highly water absorbing polymer include starch-acrylic acid graft copolymer, saponification product of starch-acrylonitrile graft copolymer, saponification product of vinyl acetate-acrylic acid ester copolymer, polyacrylic acid type polymer, polyvinyl alcohol type copolymer, cellulose glycolate, etc.

The culture carrier of the present invention for cultivation of microorganism is dried in a conventional manner, generally after incorporation of the medium components. By drying, contamination with other bacteria can be prevented and such is preferred. By setting a drying temperature, e.g., above 50° C., the carrier can be dried until the medium components are solidified to dryness in the nonwoven cloth or woven cloth, whereby contamination can be substantially completely prevented. The carrier is dried preferably above 80° C. more preferably above 100° C., for about 20 minutes. When the drying is too strong, the medium components might be denatured. However, no particular problem arises, unless cultivation of microorganisms is inconvenient.

The culture carrier of the present invention for cultivation of microorganism thus obtained is used for stationary culture as it is, or after known means of sterilization such as dry heat sterilization at about 100° C. or gas sterilization with ethylene oxide, etc.

In the present invention, vermin infectious bacteria are cultured in the thus obtained culture carrier for cultivating microorganisms to prepare the vermin exterminating element.

As the vermin infectious bacteria which are cultivated, there may be used molds such as *Beauveria tenella, Beauveria bassiana, Metarhisium anisopliae, Verticillium lecanii, Synnematium jonesii,* etc. At least one of these bacteria may be used.

By cultivating the vermin infectious bacteria described above, the culture carrrier of the present invention acts as a microbial insecticide having an excellent insecticidal effect against vermin, especially longicorn beetles, gold beetles, etc. In recent years, damage to crops by longicorn beetles tends to be increasing. In particular, damage to mulberry trees are serious and extend over a wide range. Longicorn beetles oviposit under the bark of mulberry trees. Hatched larvae make deep holes in the woody parts which causes damage and sometimes make holes of 60 cm or more. Mulberry trees having high parasitism density lose their physiological function and are sometimes blighted.

For extermination of such longicorn beetles, chemical insecticides may be applied. Since longicorn beetles are hole-making vermin, however, the insecticides do not reach larvae in the stem so that the insecticides fail to effectively exterminate the larvae. In addition, mulberry leaves are used for feeding silkworms and use of chemical insecticides adversely affects silkworms. Such chemical insecticides are also harmful to human beings and animals. It is thus not preferred to use chemical insecticides in edible trees.

The vermin exterminating element used in the present invention is not a chemical insecticide but a microbial insecticide utilizing contact infection, in which molds such as *Beauveria tenella* as a natural enemy of longicorn beetles are cultivated and brought into contact with vermin thereby to cause parasitism of the bacteria. Therefore, the foregoing problems do not occur in the present invention. In addition, the vermin infectious bacteria are cultivated in the nonwoven cloth or woven cloth so that the bacterial cells can be effectively utilized without any loss, which is preferred.

In order to culture the vermin infectious bacteria in the carrier described above, the vermin infectious bacteria are firstly inoculated on the carrier followed by cultivation at about 25° C. for about 1 to about 2 weeks. By the cultivation, the surface of carrier is covered with hyphae and spores (conidia) to give the culture carrier of the present invention for extermination of vermin. Spores (conidia) having a higher insecticidal effect against longicorn beetles than hyphae grow about $10^7$ cells or more per $cm^2$ of the surface area of nonwoven cloth. The culture carrier for cultivating microorganisms may also be impregnated with a culture solution for the vermin infectious bacteria, together with the medium components.

By cultivating the thus impregnated carrier, the vermin exterminating element may also be prepared. In this case, a solution of the medium components and the culture broth in which the vermin infectious bacteria are cultured may be directly coated to the nonwoven cloth or woven cloth or impregnated in the nonwoven cloth or woven cloth to incorporate them. By stationary culture, the bacteria may be cultivated to give the vermin exterminating element.

Upon the stationary culture, it is preferred that the vermin infectious bacteria be diluted to $10^7$ cells/ml or more, more preferably $10^8$ cells/ml or more. A ratio of the solution of the medium components to the culture solution of the vermin infectious bacteria is set to a range of 100:1 to 0.5:1, preferably in a range of 10:1 to 2:1.

It is also preferred in view of a cultivation efficiency that the solution of the medium components be used in a concentration higher than a conventionally used concentration. In particular, sugar sources are set to 10 g/l or more, preferably 20 g/l or more, more preferably in a range of 60 to 200 g/l.

The stationary culture is performed at about 25° C. and 80% R.H. or higher, or under conditions of high humidity in a closed container, for 3 days or longer, preferably for about 1 to about 2 weeks. By such cultivation, the inside or surface of the nonwoven cloth or woven cloth is covered with hyphae and spores (conidia) to give the culture carrier of the present invention for extermination of vermin.

The amount of the vermin infectious bacteria grown which are obtained by such cultivation is at least about $10^7$ cells of conidia, about $10^8$ cells or more at the highest of growth, based on 1 $cm^2$ of the nonwoven cloth. When an impregnation amount of the medium components containing the sugar sources is 70 $g/m^2$ or more, the conidial count becomes $10^8$ cells/$cm^2$ or more.

For extermination of vermin, the culture carrier of the present invention for extermination of vermin may be applied to trees, etc. as it is. Preferably, the vermin exterminating element may be dried and such is advantageous for packaging and storage.

The drying may be completed in 1 to 2 days after the cultivation, even if the element is allowed to stand at room temperature. If the bacteria are not dead, it is also possible to dry by applying air at a temperature of, e.g., 30° to 35° C., or attempting drying in a vacuum.

By drying in this manner, growth of the vermin infectious bacteria can be maintained on the highest level. The dried carrier can be stored until vermin breed; upon use, water is absorbed in the carrier thereby to activate the carrier and the activated carrier may be provided for use. If the carrier is a dried product, it is unnecessary to store under sterile conditions. The chance of decreasing the effect of exterminating vermin due to contamination with various bacteria are extremely low.

The thus obtained vermin exterminating element is used for extermination of vermin mainly against crops, e.g., longicorn beetles, etc. For extermination of vermin, the carrier is cut into an appropriate size and then sprinkled over trees such as mulberry trees, etc. In order to further improve the insecticidal effect, however, it is preferred to apply the carrier to the stem or branch of trees.

A means of application may be chosen from optional means including winding around (into, e.g., a string or strip form), latching (with, e.g., a stapler, etc.), hanging (e.g., a string or strip form) or the like. However, since the nonwoven cloth or woven cloth has a relatively thin thickness, the cloth is closely contacted even with the uneven surface of trees when the winding around means is used, whereby the efficiency of contact with the vermin is enhanced. The nonwoven cloth of the present invention may be closely contacted with and applied to trees, etc. due to its viscosity, without using any special latching means as described above, because the medium components have an adhesive property in a wet state. When good weather lasts and the nonwoven cloth is dried, the cloth is retained in the state that it was initially applied.

The culture carrier of the present invention for extermination of vermin may also be advantageously applied both to longicorn beetles and to gold beetles which also damage not only seedling fields of trees or afforested lands but also crops such as strawberries, sweet potatoes, peanuts, etc. When the infecting bacteria such as molds which are cultivated in the present invention are parasitic on imagines of gold beetles, eggs oviposited by imagines fail to be hatched, even though the imagines themselves are not exterminated.

Furthermore, in addition to the vermin described above, the culture carrier of the present invention for extermination of vermin also exhibits its effect of extermination against greenhouse whiteflies or plant lice which damage fruit trees, rice water weevils, rice insects and leafhoppers which damage rice plants and a variety of nematodes. In this case, molds other than *Beauveria tenella* or various bacteria, and *Pasteurella penetrans* as a natural enemy of nematodes may be used.

As stated hereinabove, the culture carrier for cultivating microorganisms is prepared by incorporating the medium components for cultivating microorganisms or the components and the culture solution of the vermin infectious bacteria into the nonwoven cloth or woven cloth in the present invention. Therefore, the apparent surface area is relatively large, the medium components are less flown out and a cultivation efficiency is excellent.

Furthermore, by cultivating the vermin infectious bacteria in this carrier to prepare the vermin exterminating element and contacting the cultivated infecting bacteria to exterminate vermin, the effects can be exhibited effectively without reducing the insecticidal effect as compared to conventional chemical insecticides. The vermin exterminating element does not adversely affect humans and animals. The vermin infectious bacteria are firmly carried on the carrier but are not flown out under natural environment. By applying the vermin exterminating element to the stem or branch of trees from which vermin should be exterminated, vermin such as longicorn beetles, etc. can be exterminated in a simple fashion. Moreover, since a nonwoven cloth or woven cloth is used in the present invention, a slit operation, etc. may be easily performed, and application to trees can be made in a simple manner and recovery is also simple. In addition, materials for the carrier are those having a natural degradation property. Thus, recovery after application and use in or an trees is unnecessary. Where the carrier may be absorbed into soil after natural degradation, the carrier may also be re-used as a soil modifier.

Hereafter the present invention is explained more specifically, with reference to the examples.

EXAMPLE 1

Medium components (viscosity of about 2000 centipoise) composed of 20 g of glucose, a medium prepared by extracting 40 g/l of chrysalis powders with hot water from its 3-fold concentration and 3 wt % aqueous solution of carboxymethyl cellulose (degree of etherization: 0.6 to 0.7) as a water retention agent in a proportion of 1:2 were transferred and coated onto one surface of pulp nonwoven cloth (100 g/m$^2$, 0.7 mm thick) containing 20 wt % of polyvinyl alcohol as a binder in a thickness of 1 mm. By drying at 80° C. for an hour with hot air, the culture carrier of the present invention for cultivation of microorganism was obtained.

On the other hand, mold (*Beauveria tenella*) was precultivated for 5 days while shaking, using 20 g of glucose and 400 ml of a medium obtained by extracting 40 g/l of chrysalis powder.

The culture carrier for cultivating microorganisms described above was impregnated with the culture solution and the bacteria were inoculated to perform stationary culture. The amount of the bacteria inoculated was 10$^6$ to 10$^7$ cells per cm$^2$ of the nonwoven cloth.

After cultivation at 25° C. for a week, the nonwoven cloth was observed, wherein hyphae of the mold covered the entire surface of the nonwoven cloth which was changed to white. The count of conidia excluding hyphae was 8×10$^7$ cells per cm$^2$ of the nonwoven cloth.

COMPARATIVE EXAMPLE 1

A culture carrier for cultivating microorganisms was prepared in a manner similar to Example 1 except that the medium obtained by extracting from the 3-fold concentration with hot water in Example 1 was replaced by water. Using the carrier, mold was cultivated in a manner similar to Example 1.

As the result, hyphae of the mold were not visually observed and the number of conidia was also 1.3×10$^7$ cells per cm$^2$ of the nonwoven cloth, 1 week after the cultivation.

COMPARATIVE EXAMPLE 2

In Example 1, mold was cultivated using nonwoven cloth alone, without incorporating the medium components therein. The results were similar to Comparative Example 1.

EXAMPLES 2 THROUGH 13

Mold was cultivated in a manner similar to Example 1 except that the nonwoven cloth used in Example 1 was replaced by nonwoven cloth shown in Table 1. The number of conidia one week after the cultivation is shown in Table 1. In Table 1, the results of Example 1 are also shown. As the result of cultivation for 1 week, the surface of each nonwoven cloth was covered by white hyphae.

EXAMPLES 14 THROUGH 20

Mold was cultivated in a manner similar to Example 1 except that the water retention agent used in Example 1 was replaced by a water retention agent shown in Table 2. The number of conidia one week after the cultivation is shown in Table 2. In Table 2, the number of conidia one week after the cultivation is also shown. The surface of each nonwoven cloth was covered by white hyphae one week after the cultivation.

TABLE 1

| Example: | Material | Weight g/m$^2$ | Thickness mm | Binder % | Number of Conidia cell/cm$^2$ |
|---|---|---|---|---|---|
| 1 | 100% pulp | 100 | 0.7 | PVA, 20 | 8.0 × 10$^7$ |
| 2 | " | 70 | 0.5 | " | 4.5 × 10$^7$ |
| 3 | " | 70 | 0.4 | " | 5.3 × 10$^7$ |
| 4 | " | 100 | 0.5 | " | 5.6 × 10$^7$ |
| 5 | " | 40 | 0.5 | special | 6.1 × 10$^7$ |
| 6 | Rayon/polypropylene = 80/20% | 80 | 0.8 | none | 7.1 × 10$^7$ |
| 7 | Rayon/polypropylene = 80/20% | 110 | 1.0 | " | 6.8 × 10$^7$ |
| 8 | Rayon polyester | 100 | 3.0 | — | 6.6 × 10$^7$ |
| 9 | Rayon polyester | 200 | 1.0 | — | 8.3 × 10$^7$ |
| 10 | Rayon polyester | 200 | 0.7 | — | 4.4 × 10$^7$ |
| 11 | Rayon polyester | 300 | 2.0 | — | 8.0 × 10$^7$ |
| 12 | Rayon polyester | 120 | 1.0 | — | 8.8 × 10$^7$ |
| 13 | polyester | 100 | 1.8 | — | 11.0 × 10$^7$ |

TABLE 2

| Example: | Water Retention Agent | Final Concentration (%) | Number of Conidia cell/cm$^2$ |
|---|---|---|---|
| 14 | Starch | 6.7 | 8.7 × 10$^7$ |
| 15 | Konjak | 6.7 | 5.6 × 10$^7$ |
| 16 | Starch-acrylic acid graft copolymer | 2 | 3.6 × 10$^7$ |
| 17 | Starch-acrylonitrile graft copolymer | 2 | 8.8 × 10$^7$ |
| 18 | Polyvinyl alcohol polymer | 2 | 5.7 × 10$^7$ |
| 19 | Cellulose glycolate | 13.3 | 5.5 × 10$^7$ |
| 20 | Carboxymethyl cellulose/cellulose glycolate | 2/13.3 | 5.8 × 10$^7$ |

EXAMPLE 21

Medium components were coated onto nonwoven cloth in a manner similar to Example 1 except that pulp nonwoven cloth of 40 g/m$^2$ and 0.5 mm thick containing a special binder was used as nonwoven cloth, starch-acrylonitrile graft copolymer (saponified) was used as a water retention agent and 40 g (50 wt % as solid content) of corn steep liquor was used as medium composition instead of chrysalis powder. The nonwoven cloth described above was further laminated onto the coated surface to obtain a 3-layered culture carrier for cultivating microorganisms. A thickness of the coating was 0.5 mm.

Mold was cultivated in a manner similar to Example 1, using this nonwoven cloth. The surface of the nonwoven cloth was covered by white hyphae one week after the cultivation. The number of conidia was $1.1 \times 10^8$ cells per $cm^2$ of the nonwoven cloth, 1 week after the cultivation.

EXAMPLE 22

A culture carrier for cultivating microorganisms was obtained in a manner similar to Example 21 except for using lactose instead of glucose.

Mold was cultivated in a manner similar to Example 21 except that penicillin-producing *Penicillium chrysogenum* was used as bacteria cultivated, instead of *Beauveria tenella*. The surface of the nonwoven cloth was covered by green hyphae and conidia one week after the cultivation. The number of conidia was $1.0 \times 10^8$ cells per $cm^2$ of the nonwoven cloth.

EXAMPLE 23

The culture carrier for cultivating microorganisms obtained in Example 22 was cut into small pieces of 5 mm each and 50 pieces were put in 100 ml of distilled water. One platinum ear loop of *Penicillium chrysogenum* (conidia) was inoculated thereon followed by shake culture. Hyphae grew on the surface of the nonwoven cloth and in the liquid leaked out thereby to produce penicillin. Its amount was 500 to 1000 mg/l.

EXAMPLE 24

Nonwoven cloth (100 g/m², 3 mm thick) made of rayon and polyester was immersed in and impregnated with medium components composed of 20 g of glucose, medium obtained by extracting 40 g/l of chrysalis powders with hot water and 1.5 wt % of agar as a water retention agent, which was sterilized in an autoclave for 20 minutes at 120° C. under 1.2 atm. After sterilization, the culture was transferred to a sterile Petri dish and subjected to natural seasoning in a clean bench overnight to prepare a culture carrier for cultivating microorganisms.

Using the nonwoven cloth, mold was cultured in a manner similar to Example 1. One week after the cultivation, the surface of the nonwoven cloth was covered with white hyphae. The number of conidia per $cm^2$ was $4.7 \times 10^7$ cells.

COMPARATIVE EXAMPLE 3

Mold was cultivated in a manner similar to Example 24 except for using water as the medium component. Hyphae of the mold were not visually observed and the number of conidia was $4.2 \times 10^6$ cells per $cm^2$ of the nonwoven cloth.

EXAMPLE 25

The medium components of Example 1 were inserted into two laminated sheets of the nonwoven cloth-made culture carrier for cultivating microorganisms obtained in Example 1 to prepare a laminated culture carrier for cultivating microorganisms. The coated amount of the medium components after drying was about 36 g/m².

Using the nonwoven cloth, mold was subjected to stationary culture in a manner similar to Example 1. One week after the cultivation, the entire surface of the nonwoven cloth was covered with hyphae and turned white. In this case, the number of conidia excluding hyphae was $7.3 \times 10^7$ cells per $cm^2$ of the nonwoven cloth.

COMPARATIVE EXAMPLE 4

Mold was cultivated for a week in a manner similar to Example 1 except that water was used instead of the medium obtained by 3-fold concentration hot water extraction in Example 25.

As a result, hyphae could not visually be observed on the nonwoven cloth and the number of conidia was $1.1 \times 10^7$ cells per $cm^2$ of the nonwoven cloth.

EXAMPLES 26 AND 27

Mold was cultivated in a manner similar to Example 25 except that the nonwoven cloth used in Example 25 was replaced by nonwoven cloth shown in Table 3. The number of conidia one week after the cultivation is shown in Table 3. In Table 3, the results of Example 25 are also shown. As the result of cultivation for 1 week, the surface of each nonwoven cloth was covered by white hyphae.

TABLE 3

| Example: | Material | Weight g/m² | Thickness mm | Binder % | Number of Conidia cell/cm² |
|---|---|---|---|---|---|
| 25 | 100% pulp | 100 | 0.7 | PVA, 20 | $7.3 \times 10^7$ |
| 26 | " | 40 | 0.5 | special | $8.0 \times 10^7$ |
| 27 | Rayon polyester | 100 | 3.0 | — | $7.4 \times 10^7$ |

EXAMPLES 28 THROUGH 31

Mold was cultivated in a manner similar to Example 25 except that the water retention agent used in Example 25 was replaced by a water retention agent shown in Table 4. The number of conidia one week after the cultivation is shown in Table 4. One week after the cultivation, the surface of each nonwoven cloth was covered by white hyphae.

TABLE 4

| Example: | Water Retention Agent | Final Concentration (%) | Number of Conidia cell/cm² |
|---|---|---|---|
| 28 | Starch-acrylic acid graft copolymer | 2 | $3.6 \times 10^7$ |
| 29 | Starch-acrylonitrile graft copolymer | 2 | $2.5 \times 10^7$ |
| 30 | Polyvinyl alcohol polymer | 2 | $5.7 \times 10^7$ |
| 31 | Cellulose glycolate | 13.3 | $5.5 \times 10^7$ |

EXAMPLE 32

Figure 1:
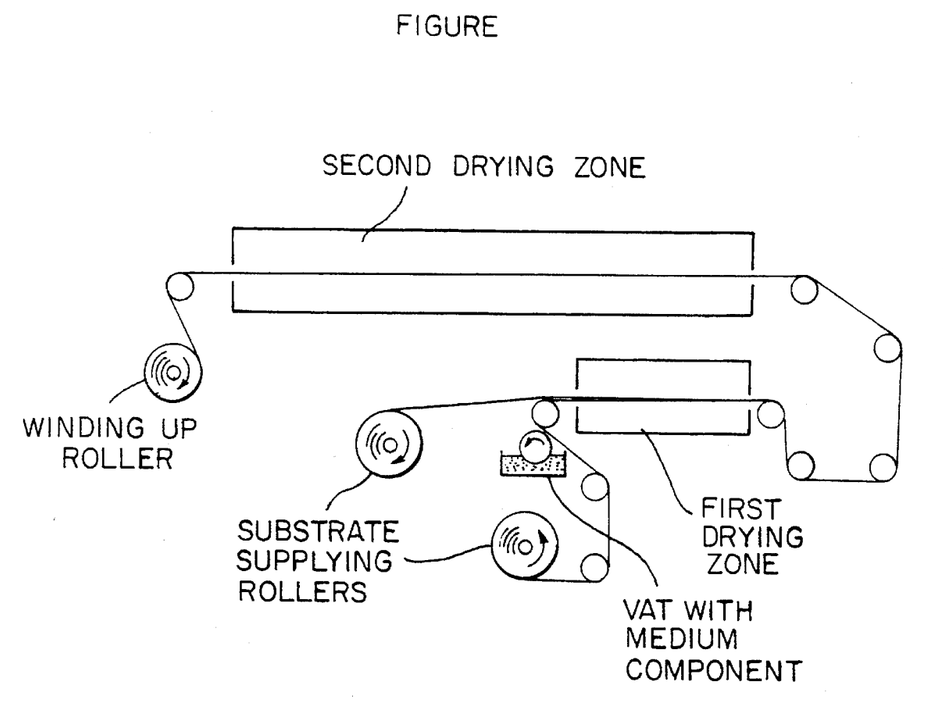
FIG. 1 is an outline of application step used in Examples 32 and 35.

The culture carrier for cultivating microorganisms in Example 21 was coated using a coating machine. The outlined steps using the coating machine are shown in FIG. 1. The coating was performed at 1.2 m/min both in a controlled rotary speed and a coating speed in a coating width of 50 cm, using a kiss coater. Drying was performed at 100° C. for about minutes at a first drying zone and at a second drying zone, at 100° C. for about 25 minutes. After the first coating was completed, the nonwoven cloth was wound up and then laminated by again coating. The amount of the medium coated was 36±10 g/m$^2$.

The resulting nonwoven cloth was slit into an appropriate size and mold was cultivated therein in a manner similar to Example 21. By the cultivation for 1 week, the entire surface of the nonwoven cloth was almost uniformly covered with hyphae and turned white. In this case, the number of conidia excluding hyphae was 2.0 to 4.7×10$^7$ cells per cm$^2$ of the nonwoven cloth.

EXAMPLE 33

Imagines (one each of male and female) of cryptomeria bark borers or *Semanotus japnicus* (Lacordaire) of 3 to 5 days age after emergence were locomoted on the vermin exterminating element obtained in Example 25 for one minute, respectively.

After the locomotion, the imagines were fed with honey and water and breeding was continued at 22° C. The male insect died on Day 6 and the female died on Day 7. While the female was oviposited during the course of breeding, its eggs were covered with hyphae but failed to hatch. The dead bodies of the both male and female cryptomeria bark borers or *Semanotus japnicus* (Lacordaire) were subjected to a surface treatment with 70% alcohol and put in a plate together with filter paper impregnated with distilled water, which was stored at 24° C. It was noted that *Beauveria tenella* was locally developed at the joints of the bodies.

EXAMPLE 34

A test was performed on imagines of yellowspotted longicorn beetles or *Psacothea hiraris* (Pascoe) in a manner similar to Example 33, using the vermin exterminating element obtained in Example 21.

As a result, the yellowspotted longicorn beetles died 10 days after and the body surface was covered with *Beauveria tenella* 3 days after the death.

EXAMPLE 35

The vermin exterminating element of Example 21 was treated in a manner similar to Example 32, using a coating machine.

The resulting nonwoven cloth was cut into a length of 1 m. Several strips of the cut nonwoven cloth were suitably entangled with each other and disposed on a mandarine orange tree in a net room by hanging it at the branched portion of the tree. Then, ten (10) imagines of whitespotted longicorn beetles or *Anoplophora malasiaca* (Thomson) were released in the net room.

One week after, the nonwoven cloth maintained its disposed condition. Further five (5) imagines of whitespotted longicorn beetles or *Anoplophora malasiaca* (Thomson) were locomoted on the nonwoven cloth for 1 minutes. After the locomotion, all of the whitespotted longicorn beetles were recovered. The ten (10) whitespotted longicorn beetles initially released died in one week and the locomoted five (5) whitespotted longicorn beetles died in 15 days.

In these dead whitespotted longicorn beetles, the body surface was covered with *Beauveria tenella* 3 days after the death.

COMPARATIVE EXAMPLE 5

In Example 33, imagines of cryptomeria bark borers or *Semanotus japnicus* (Lacordaire) were not locomoted on the vermin exterminating element. The insects were still alive even after 15 days passed.

COMPARATIVE EXAMPLE 6

In Example 34, imagines of yellowspotted longicorn beetles or *Psacothea hiraris* (Pascoe) were not locomoted on the vermin exterminating element. The insects were still alive even after 30 days passed.

COMPARATIVE EXAMPLE 7

In Example 35, imagines of whitespotted longicorn beetles or *Anoplophora malasiaca* (Thomson) were not brought into contact with the vermin exterminating element. The insects were still alive even after 40 days passed.

EXAMPLE 36

A mixture of 1 liter of the culture solution obtained by preincubation of mold (*Beauveria tenella*) in 20 g/l of glucose and a medium solution obtained by extracting 40 g/l of chrysalis powders while shaking for 5 days and 4 liters of 100 g/l of glucose and 40 g/l of chrysalis powders was poured onto the surface of pulp nonwoven cloth (300 g/m$^2$, 5.0 mm thick) containing a starch water absorbent (20 g/m$^2$) to sufficiently impregnate therewith.

The nonwoven cloth was put in a polypropylene bag followed by stationary culture at 25° C. for a week. The nonwoven cloth was then observed. The entire surface of the nonwoven cloth was covered with hyphae of the mold and turned white. In this case, the number of conidia excluding hyphae was 2×10$^8$ cells per cm$^2$ of the nonwoven cloth.

COMPARATIVE EXAMPLE 8

A polyurethane foam was prepared by reacting 100 g of Sofranate (trademark, manufactured by Toyo Tire and Rubber Co., Ltd.) with 275 g of 5 wt % gelatin aqueous solution.

The foam was cut into a size of 5 mm thick and impregnated with the preincubation solution of mold in a manner similar to Example 36. Subsequently, stationary culture was performed in a manner similar to Example 36 to proliferate the bacteria.

The entire surface was covered with hyphae. The number of conicia excluding hyphae was 4±10$^7$ cells per cm$^2$ of the foam.

EXAMPLE 37

Cultivation was carried out in a manner similar to Example 36 except that fructose was used instead of glucose. One week after, the number of conidia excluding hyphae was 2×10$^8$ cells or greater, per cm$^2$ of the nonwoven cloth.

EXAMPLE 39

After cultivation of the vermin exterminating element obtained in Example 36, the element was withdrawn from a bag and air-dried at room temperature for a day. The number of conidia of the dried element excluding hyphae was 2×10$^8$ cells or greater, per cm$^2$ of the nonwoven cloth.

EXAMPLES 40 THROUGH 45

Cultivation was carried out in a manner similar to Example 36 except that the nonwoven cloth was replaced with those shown in Table 5.

One week after, the number of conidia excluding hyphae is also shown in Table 5. As the result of cultivation for a week, the surface of each nonwoven cloth was covered with white hyphae.

TABLE 5

| Example: | Material | Weight g/m² | Thickness mm | Binder % | Number of Conidia cell/cm² |
|---|---|---|---|---|---|
| 40 | 100% pulp | 100 | 0.7 | PVA, 20 | $1.2 \times 10^8$ |
| 41 | " | 40 | 0.5 | special | $0.9 \times 10^8$ |
| 42 | Rayon/polypropylene = 80/20% | 80 | 1.0 | none | $1.0 \times 10^8$ |
| 43 | Rayon polyester | 100 | 3.0 | — | $1.1 \times 10^8$ |
| 44 | Rayon polyester | 300 | 2.0 | — | $1.2 \times 10^8$ |
| 45 | polyester | 100 | 1.8 | — | $1.5 \times 10^8$ |

EXAMPLE 46

A mixture of 1 liter of the preculture solution of *Beauveria tenella* and 2 liters of medium solution of 40 g/l of glucose and 50 g/l of corn steep liquor was poured onto the surface of pulp nonwoven cloth (400 g/m², 6.5 mm thick) containing a starch water absorbent (30 g/m²) to sufficiently impregnate therewith.

After the nonwoven cloth was subjected to stationary culture at 25° C. for a week under humidity of 95% R.H., the nonwoven cloth was observed. The entire surface of the nonwoven cloth was covered with hyphae of the mold and turned white. After air drying at 30° C. for 6 hours under 30% R.H., the number of conidia excluding hyphae was $2.3 \times 10^8$ cells per cm² of the nonwoven cloth.

EXAMPLE 47

Cultivation was carried out in a manner similar to Example 37 except for using *Verticillium lecanii* instead of *Beauveria tenella*. One week after, the number of conidia excluding hyphae was $1 \times 10^8$ cells or greater, per cm² of the nonwoven cloth. *Verticillium lecanii* was superior to *Beauveria tenella* in elongation of hyphae more than in growth of conidia.

EXAMPLE 48

Imagines (one each of male and female) of cryptomeria bark borers or *Semanotus japnicus* (Lacordaire) of 3 to 5 days age after emergence were locomoted on the vermin exterminating element obtained in Example 36 for one minute, respectively.

After the locomotion, the imagines were fed with honey and water, and breeding was continued at 22° C. The male insect died on Day 6 and the female died on Day 7. While the female was oviposited during the course of breeding, its eggs were covered with hyphae but failed to hatch. The dead bodies of the both male and female cryptomeria bark borers or *Semanotus japnicus* (Lacordaire) were subjected to a surface treatment with 70% alcohol and put in a plate together with filter paper impregnated with distilled water, which was stored at 24° C. It was noted that *Beauveria tenella* was locally developed at the joints of the bodies.

EXAMPLE 49

A test was performed on imagines of yellowspotted longicorn beetles or *Psacothea hiraris* (Pascoe) in a manner similar to Example 48, using the vermin exterminating element obtained in Example 39.

As a result, the yellowspotted longicorn beetles or *Psacothea hiraris* (Pascoe) died 10 days after and the body surface was covered with *Beauveria tenella* 3 days after the death.

EXAMPLE 50

The vermin exterminating element of Example 36 was cut into a length of 1 m. Several strips of the cut nonwoven cloth were suitably entangled with each other and disposed on a mandarine orange tree in a net room by hanging it at the branched portion of the tree. Then, ten (10) imagines of whitespotted longicorn beetles or *Anoplophora malasiaca* (Thomson) were released in the net room.

One week after, the nonwoven cloth maintained its disposed condition. Further five (5) imagines of whitespotted longicorn beetles or *Anoplophora malasiaca* (Thomson) were locomoted on the nonwoven cloth for 1 minutes. After the locomotion, all of the whitespotted longicorn beetles were recovered. The ten (10) whitespotted longicorn beetles initially released died in one week and the locomoted five (5) whitespotted longicorn beetles died in 15 days.

In these dead whitespotted longicorn beetles, the body surface was covered with *Beauveria tenella* 3 days after the death.

COMPARATIVE EXAMPLE 9

In Example 48, imagines of cryptomeria bark borers or *Semanotus japnicus* (Lacordaire) were not locomoted on the vermin exterminating element. The insects were still alive even after 15 days passed. The eggs oviposited by the female cryptomeria bark borers or *Semanotus japnicus* (Lacordaire) were all hatched.

COMPARATIVE EXAMPLE 10

In Example 49, imagines of yellowspotted longicorn beetles or *Psacothea hiraris* (Pascoe) were not locomoted on the vermin exterminating element. The insects were still alive even after 30 days passed.

COMPARATIVE EXAMPLE 11

In Example 50, imagines of whitespotted longicorn beetles or *Anoplophora malasiaca* (Thomson) were not brought into contact with the vermin exterminating element. The insects were still alive even after 40 days passed.

EXAMPLE 51

The dried vermin exterminating element obtained in Example 46 was immersed in sterile water dissolved in 20 g/l of glucose therein to impregnate with water. The element was put in a polypropylene and allowed to stand at room temperature for 3 days.

A test was performed with the bag in a manner similar to Example 49. The yellowspotted longicorn beetles or *Psacothea hiraris* (Pascoe) died in 7 to 14 days and the body surface was covered with *Beauveria tenella* 3 days after the death.

EXAMPLE 52

A test was carried out with the preincubation medium used in Example 36 in a manner similar to Example 51. As a result, the results similar to this Example were obtained.

EXAMPLE 53

The vermin exterminating element obtained in Example 47 was used for a test similar to Example 48. As a result, imagines of both male and female cryptomeria bark borers or *Semanotus japnicus* (Lacordaire) were alive for 15 days or longer. However, the eggs oviposited by the female during the breeding were covered with mold or *Verticillium lecanii* but not hatched.

EXAMPLE 54

A plurality of cotton woven cloth sheets were used instead of the pulp nonwoven cloth and laminated with each other to render its thickness about 5 mm, which was sawed with a sawing machine. Mold was cultivated in the laminated woven cloth in a manner similar to Example 36 to give the results similar to those in Example 36. The number of conidia excluding hyphae was $1.5\times10^8$ cells per $cm^2$ of the nonwoven cloth.

EXAMPLE 55

Mold was cultivated in a manner similar to Example 54 using woven cloth of 50% linen and 50% cotton. The results similar to those in Example 54 were obtained.

EXAMPLE 56

The dried element obtained in a manner similar to Example 39 was stored at 5° C. and examined in a manner similar to Example 49. The results similar to those in Example 49 were obtained.

EXAMPLE 57

The dried element obtained in a manner similar to Example 39 was stored at 32° C. for 14 days and examined in a manner similar to Example 49. The results similar to those in Example 49 were obtained.

COMPARATIVE EXAMPLE 12

The culture carrier obtained in Example 36 was stored at 32° C. for 10 days in a wet state and examined in a manner similar to Example 48. The results similar to Comparative Example 10 were obtained.

EXAMPLE 58

The dried element obtained in a manner similar to Example 39 was stored at 25° C. for 40 days and examined in a manner similar to Example 49. The results similar to those in Example 49 were obtained.

While the invention has been adequately and sufficiently described, changes and modifications within the spirit and scope of this invention should be understood.

We claim:

1. A vermin exterminating element comprising a culture carrier which comprises nonwoven cloth or woven cloth coated or impregnated with medium components for cultivating a microorganism and with a culture solution of a vermin infectious microorganism, wherein said vermin exterminating element is dried after cultivating said vermin infectious microorganism, and said nonwoven cloth or woven cloth has a thickness of 1.8 mm or more and has a base weight of at least 100 $g/m^2$.

2. The vermin exterminating element according to claim 1, wherein the vermin exterminating element comprises a plurality of layers of the nonwoven cloth or woven cloth which are laminated together and the medium components for cultivating a microorganism are inserted between the plurality of layers as adhesive components.

3. The vermin exterminating element according to claim 1, wherein a hydrophilic polymer is incorporated therein.

4. The vermin exterminating element according to claim 3, wherein the hydrophilic polymer is selected from the group consisting of agar, polyvinyl alcohol, polyacrylamide, starch, konjak mannan, carboxymethylcellulose, polyacrylic acid, polyacrylonitrile and alginic acid.

5. The vermin exterminating element according to claim 3, wherein the hydrophilic polymer is a highly water-absorbing polymer selected from the group consisting of starch-acrylic acid graft copolymer, saponification product of starch-acrylonitrile graft copolymer, saponification production of vinyl acetate-acrylic acid ester copolymer, polyacrylic acid polymer, polyvinyl alcohol copolymer, and cellulose glycolate.

6. The vermin exterminating element according to claim 1, wherein the vermin infectious microorganism is mold.

7. The vermin exterminating element according to claim 6, wherein the mold is at least one mold selected from the group consisting of *Beauveria tenella, Beauveria bassiana, Metarhizium anisopliae, Verticillium lecanii* and *Synnematium jonesii.*

8. The vermin exterminating element according to claim 1, wherein the nonwoven cloth is selected from the group consisting of pulp, rayon and polyester.

9. The vermin exterminating element according to claim 1, wherein the medium components are coated or impregnated in an amount of at least 10 $g/m^2$ of the carrier.

10. The vermin exterminating element according to claim 1, wherein the medium components are coated or impregnated in an amount of 20 to 70 $g/m^2$ of the carrier.

11. The vermin exterminating element according to claim 1, wherein the medium components have a viscosity adjusted to at least 10 centipoise.

12. The vermin exterminating element according to claim 1, wherein the medium components have a viscosity of $10^2$ to $10^4$ centipoise.

13. The vermin exterminating element according to claim 1, wherein the vermin infectious microorganism culture solution is inside the nonwoven cloth.

14. The vermin exterminating element according to claim 1, wherein the vermin infectious microorganism culture solution is on a surface of the nonwoven cloth.

15. The vermin exterminating element according to claim 1, wherein said thickness is 3.0 mm or more.

16. The vermin exterminating element according to claim 1, wherein said thickness is 2.0 mm or more and said base weight is at least 300 $g/m^2$.

17. The vermin exterminating element according to claim 1, wherein the nonwoven cloth or woven cloth has a base weight in the range of 100 to 200 $g/m^2$.

18. The vermin exterminating element according to claim 1, wherein said thickness is 5.0 mm or more and said base weight is at least 300 $g/m^2$.

19. A method for exterminating vermin which comprises applying a vermin exterminating element to a stem or branch of a tree from which vermin are to be exterminated, wherein said vermin exterminating element comprises a culture carrier which comprises nonwoven cloth or woven cloth impregnated with medium components for cultivating a microorganism, wherein a culture solution of a vermin infectious microorganism is impregnated together with the medium components, wherein said vermin exterminating element is dried after cultivating said vermin infectious microorganism, and said nonwoven or woven cloth has a thickness of 1.8 mm or more and has a base weight of at least 100 g/m$^2$.

* * * * *